United States Patent
Mark et al.

(10) Patent No.: US 8,096,314 B2
(45) Date of Patent: Jan. 17, 2012

(54) FLUIDIC DEVICE, FLUIDIC MODULE, AND METHOD OF HANDLING A LIQUID

(75) Inventors: Daniel Mark, Freiburg (DE); Stefan Haeberle, St. Georgen (DE); Felix Von Stetten, Freiburg (DE); Jens Ducree, Dublin (IE)

(73) Assignee: Hahn-Schickard-Gesellschaft fuer angewandte Forschung e.V., Villingen-Schwenningen (DE)

( * ) Notice: Subject to any disclaimer, the term of this patent is extended or adjusted under 35 U.S.C. 154(b) by 572 days.

(21) Appl. No.: 12/350,281

(22) Filed: Jan. 8, 2009

(65) Prior Publication Data
US 2010/0307595 A1    Dec. 9, 2010

(30) Foreign Application Priority Data
Jan. 11, 2008  (DE) .......................... 10 2008 003 979

(51) Int. Cl.
*F17D 3/00* (2006.01)
*F04B 19/00* (2006.01)
(52) U.S. Cl. ............................... 137/1; 137/38; 422/506
(58) Field of Classification Search ................ 137/1, 38; 422/506
See application file for complete search history.

(56) References Cited

U.S. PATENT DOCUMENTS

| | | | |
|---|---|---|---|
| 4,287,523 A * | 9/1981 | Thomas et al. ................. | 137/38 |
| 6,506,344 B1 | 1/2003 | Fickenscher et al. | |
| 7,935,318 B2 * | 5/2011 | Harding ........................ | 422/502 |
| 7,988,915 B2 * | 8/2011 | Lee et al. ...................... | 422/506 |
| 2002/0027133 A1 | 3/2002 | Kellogg et al. | |
| 2003/0207457 A1 | 11/2003 | Kopf-Sill et al. | |

FOREIGN PATENT DOCUMENTS

| | | |
|---|---|---|
| DE | 198 52 835 A1 | 5/2000 |
| EP | 1 359 415 A1 | 11/2003 |
| WO | 2006/110098 A1 | 10/2006 |

OTHER PUBLICATIONS

Haeberle et al.: "Microfluic Platforms for Lab-on-a-Chip Applications," Lab on a Chip; Institute for Micromachining and Information Technology; Jul. 27, 2007; 25 pages.
Zoval et al.: "Centrifuge-Based Fluidic Platforms," Proceedings of the IEEE; vol. 92; No. 1; Jan. 2004; pp. 140-153.
Madou et al.: "Lab on a CD," Annual Review of Biomedical Engineering; vol. 8; May 2, 2006; pp. 601-628.
Duffy et al: "Microfabricated Centrifugal Microfluidic Systems: Characterizations and Multiple Enzymatic Assays," Analytical Chemistry; vol. 71; No. 20; Sep. 11, 1999; pp. 4669-4678.
Schembri et al.: "Centrifugation and Capillarity Integrated Into a Multiple Analyte Whole Body Analyser," Journal of Automatic Chemistry; vol. 17, No. 3; May-Jun. 1995; pp. 99-104.

(Continued)

*Primary Examiner* — Kevin Lee
(74) *Attorney, Agent, or Firm* — Keating & Bennett, LLP

(57) ABSTRACT

A fluidic device includes a fluidic module with a first fluid chamber and a second fluid chamber closed with the exception of a fluidic connection to the first fluid chamber. A drive is formed to impart the fluidic module with a first rotation at a rotational frequency below a rotational frequency threshold at which liquid is pneumatically held in the first fluid chamber and does not enter the second fluid chamber. The drive is further formed to impart the fluidic module with a second rotation at a second rotational frequency above the rotational frequency threshold at which a liquid column created in the first fluid chamber becomes unstable and the liquid enters the second fluid chamber.

20 Claims, 5 Drawing Sheets

OTHER PUBLICATIONS

Ducree et al.: "The Centrifugal Microfluidic Bio-Disk Platform," Journal of Micromechanics and Microengineering; vol. 17, No. 7; Jun. 28, 2007; pp. S103-S115.

Chen et al.: "Total Nucleic Acid Analysis Integrated on Microfluidic Devices," Lab on a Chip; Aug. 9, 2007; pp. 1413-1423.

Honda et al.: "Simultaneous on Multiple Immunoassays in a Compact Disc-Shaped Microfluic Device Based on Centrifugal Force," Clinical Chemistry; vol. 51, No. 10; Oct. 2005; pp. 1955-1961.

Cho et al.: "One-Step Pathogen Specific DNA Extraction From Whole Blood on a Centrifugal Microfluidic Device," Lab on a Chip; vol. 7, No. 5; Feb. 15, 2007; pp. 565-573.

Sharp: "An Overview of Rayleigh-Taylor Instability," Physica D; vol. 12, No. 1-3; 1984; pp. 3-18.

Plesset et al.: "General Analysis of the Stability of Superposed Fluids," American Institute of Physics; vol. 7, No. 8; Aug. 1964; pp. 1099-1108.

Steigert et al.: "Rapid Prototyping of Microfluidic Chips in COC," Journal of Micromechanics and Microengineering; vol. 17, No. 2; Jan. 11, 2007; pp. 333-341.

Official Communication issued in corresponding Application No. GB0900247.8, dated on May 14, 2009.

* cited by examiner

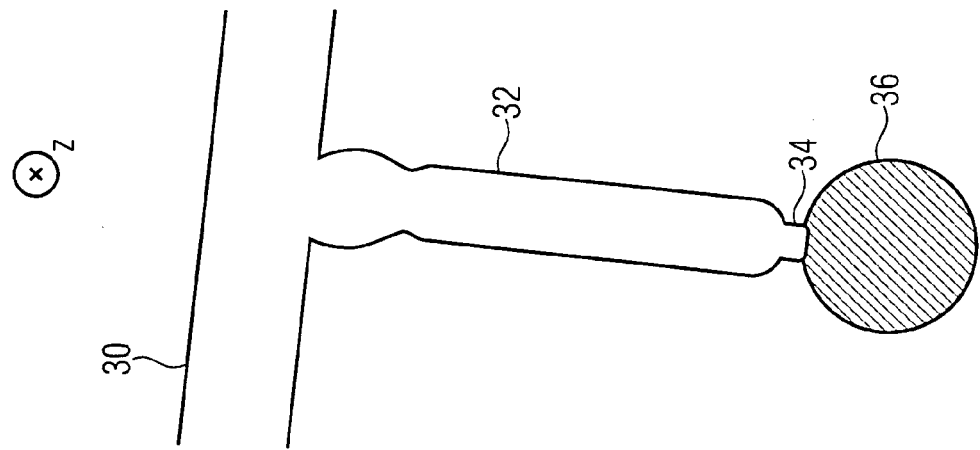
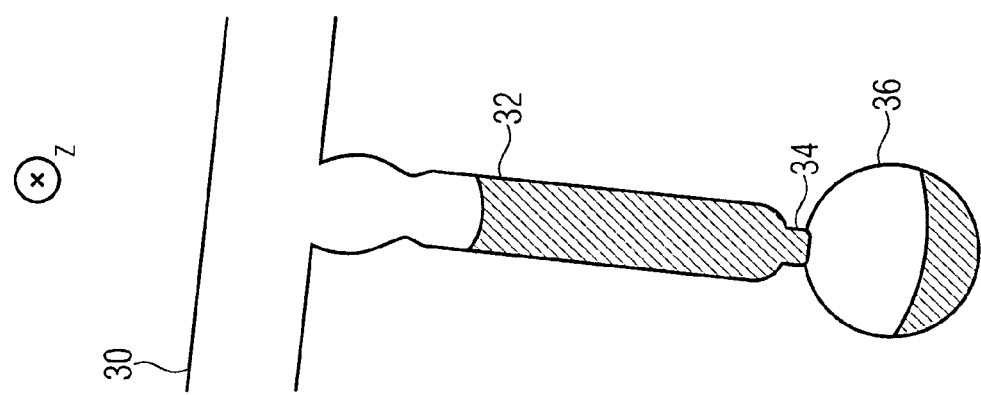
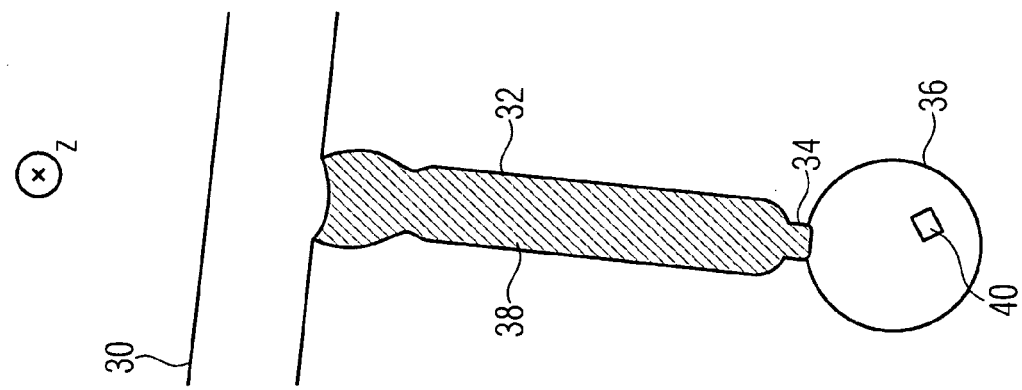

US 8,096,314 B2

FLUIDIC DEVICE, FLUIDIC MODULE, AND METHOD OF HANDLING A LIQUID

CROSS-REFERENCE TO RELATED APPLICATIONS

This application claims priority from German Patent Application No. 10 2008 003 979.9, which was filed on Jan. 11, 2008, and is incorporated herein in its entirety by reference.

BACKGROUND OF THE INVENTION

The present invention relates to a fluidic device, a fluidic module, and a method of handling a liquid, which are suited in particular to fill a fluid chamber that is closed with the exception of a fluidic access with liquid.

In centrifugal microfluidics, the centripetal acceleration of a disk under rotation is used to transport and control liquid amounts in the nanoliter to milliliter range in controlled manner. The liquid transport usually is done in channels on the disk having characteristic dimensions in the micrometer to millimeter range.

Examples of such microfluidic platforms are described in S. Haeberle and R. Zengerle, "Microfluidic Platforms for Lab-on-a-Chip Applications", *Lab Chip*, p. 1094-1110, 2007; J. V. Zoval et al., "Centrifuge-based fluidic platforms", *Proceedings of the IEEE*, Vol. 92, No. 1, p. 140-153, January 2004; J. Ducrée et al., "The centrifugal microfluidic Bio-Disk platform", *Journal of Micromechanics and Microengineering*, Vol. 17, No. 7, p. S103-S115, 2007; and M. Madou et al., "Lab on a CD", *Annual Review of Biomedical Engineering*, Vol. 8, p. 601-628, 2006.

Typical applications of centrifugal microfluidics are in the life sciences and in medical diagnostics. Advantages of the centrifugal microfluidics are based on the improved integration, automation, miniaturization and parallelization of process flows by means of application-specific cartridges that may be played in a multi-purpose device in the ideal case. Many methods may necessitate switching, dosing and distributing a sample, the so-called aliquoting, for subsequently performing some parallel experimentation steps. After the aliquoting, the sample then reacts with reagents specifically provided in the respective channels, in many applications.

Aliquoting of partial samples by combination of hydrophilic channels with hydrophobic zones is described in WO-A1-2004/083108. Aliquoting via a centrifugally filled distribution channel is described in U.S. Pat. No. B2-6,752, 961. The dosed volume here substantially corresponds to the geometry of a certain structural portion. Here, reliable division into partial volumes defined independently of the volumes of the substances provided in channel portions after the dividing structure is desirable. Moreover, the liquids in the reaction chambers should be separated in fluidically clean manner after the splitting in order to avoid penetration of the upstream substances into other reaction chambers.

For controlling processes on a disk, up to now there are several possibilities to stop or let liquids pass again at controlled points and at controlled times. One example is generating a local hydrophobization with or without simultaneous shrinkage of the channel width, as described in M. Madou et al., "Lab on a CD", *Annual Review of Biomedical Engineering*, Vol. 8, p. 601-628, 2006. In this method, the flow is counteracted by a flow barrier caused via the interfacial tension and only exceeded starting at a certain centrifugal acceleration. A further possibility for stopping liquids is an abrupt and sharp-edged channel expansion in a hydrophilic channel, at it is described in D. C. Duffy et al., "Microfabricated centrifugal microfluidic systems: Characterization and multiple enzymatic assays", *Analytical Chemistry*, Vol. 71, No. 20, p. 4669-4678, October 1999. Here, a resistance, which again is overcome only starting at a certain rotational frequency, is presented to the further flow by the superficial tension of the water.

Another known possibility of temporarily stopping liquids are siphon structures, for example see C. T. Schembri et al., "Centrifugation and Capillarity Integrated Into A Multiple Analyte Whole-Blood Analyzer", *Journal of Automatic Chemistry*, Vol. 17, No. 3, p. 99-104, May 1995. Here, at first capillary filling of a siphon-shaped structure is suppressed by an adverse centrifugal field. If the rotational frequency drops below a certain threshold, the siphon is filled capillarily, and the leading meniscus may sink radially outside the liquid level in the upstream reservoir. A higher rotational speed then subsequently conveys the liquid further. The siphon additionally may be filled by the inlet-side addition of a displacement volume.

Apart from the basically reusable valves mentioned, there also exist so-called sacrificial valves, which cannot be used again after a single actuation. One example of such valves is barriers of wax or thin foils in the flow channel, which are melted by a laser and thus allow for the flow. In this respect, reference can be made, for example, to Y. K. Cho et al., "One-step pathogen specific DNA extraction from whole blood on a centrifugal microfluidic device", *Lab on a Chip*, Vol. 7, No. 5, p. 565-573, February 2007.

SUMMARY

According to an embodiment, a fluidic device may have: a fluidic module having a first fluid chamber with a fluid outlet, a second fluid chamber with a fluidic access, and a fluidic connection between the fluid outlet of the first fluid chamber and the fluidic access of the second fluid chamber, wherein the second fluid chamber is fluidically connected only to the first fluid chamber and otherwise is fluidically closed; and a drive formed to impart the fluidic module with a first rotation at a rotational frequency below a rotational frequency threshold and a second rotation at a rotational frequency above the rotational frequency threshold, wherein the first and second fluid chambers and the fluidic connection are formed such that, in the case of rotation at a rotational frequency below the rotational frequency threshold, a fluidic closure is formed by the liquid at the fluidic access to the second fluid chamber, and a liquid column having a radially exterior meniscus on which gas located in the second fluid chamber exerts a back pressure decisive for the liquid column to remain stable is generated in the first fluid chamber, and in the case of rotation at a rotational frequency above the rotational frequency threshold, the liquid column becomes unstable so that liquid enters the second fluid chamber and gas escapes through the liquid column.

According to another embodiment, a fluidic module for such a fluidic device may have: a first fluid chamber with a fluid outlet; a second fluid chamber having a fluidic access; a fluidic connecting channel between the fluid outlet of the first fluid chamber and the fluidic access of the second fluid chamber, wherein the second fluid chamber is fluidically connected only to the first fluid chamber and otherwise is fluidically closed, wherein the first and second fluid chambers and the fluidic connection are formed such that, in the case of rotation at a rotational frequency below the rotational frequency threshold, a fluidic closure is formed by the liquid at the fluidic access to the second fluid chamber, and a liquid column having a radially exterior meniscus on which gas located in the second fluid chamber exerts a back pressure decisive for the liquid column to remain stable is generated in the first fluid chamber, and, in the case of rotation at a rotational frequency above the rotational frequency threshold, the liquid column becomes unstable so that liquid enters the second fluid chamber and gas escapes through the liquid column, wherein there are provided a plurality of azimuthally distributed fluidic structures each having a first fluid chamber, a fluidic connection, and a second fluid chamber, wherein radially interior ends of the first fluid chambers of the fluidic structures are fluidically connected to a common radially falling distribution channel, wherein the plurality of second fluid chambers of the fluidic structures are arranged on a line concentrical with a rotation axis about which the fluidic module is rotatable, and wherein the plurality of azimuthally distributed first fluid chambers of the fluidic structures have different lengths in radial direction, wherein a first fluid chamber longer in radial direction has a smaller width in azimuthal direction, in order to adapt the chamber volumes of the first fluid chambers to each other.

According to another embodiment, a method of handling a liquid in a fluidic module having a first fluid chamber with a fluid outlet, a second fluid chamber with a fluidic access, and a fluidic connection between the fluid outlet of the first fluid chamber and the fluidic access of the second fluid chamber, wherein the second fluid chamber is radially connected only to the first fluid chamber and otherwise is fluidically closed, may have the steps of: rotating the fluidic module at a rotational frequency below a rotational frequency threshold for creating a fluidic closure by the liquid at the fluidic access to the second fluid chamber and for creating a liquid column in the first fluid chamber, which has a radially exterior meniscus, on which gas located in the second fluid chamber exerts a back pressure decisive for the liquid column to remain stable; and then rotating the fluidic module at a rotational frequency above the rotational frequency threshold such that the liquid column becomes unstable so that liquid enters the second fluid chamber and gas escapes through the liquid column.

Embodiments of the present invention thus provide a novel method of switching liquids, wherein the corresponding fluidic structures may also be referred to as switches or valves. Embodiments of fluidic structures according to the invention may include a radially interior first fluid chamber, a radially exterior second fluid chamber, and a connection, for example a constriction, at which a meniscus may be built up and stabilized up to a certain rotational frequency. The radially interior fluid chamber may here be formed by a channel structure. The radially exterior fluid chamber does not comprise any further outlet for fluids. In embodiments, reagents may be provided in wet or dry fashion in the radially exterior chamber. In embodiments of the invention, a microarray that may comprise capture structures for constituents included in the liquid to be switched may be provided in the radially exterior chamber. In general, means for analyzing the liquid may be included in the second fluid chamber. The switching process is controlled via the interplay of structural geometry, interfacial tension and inertial forces, as well as the centrifugal field induced by the rotational movement (rotation-induced inertial force).

In embodiments of the invention, the geometry of the first fluid chamber, the fluidic connection and the second fluid chamber is designed such that a liquid is held in the first fluid chamber pneumatically by way of gas pressure present in the second fluid chamber in the case of rotation at a rotational frequency below a rotational frequency threshold, and liquid from the first fluid chamber enters the second fluid chamber in the case of rotation at a rotational frequency above the rotational frequency threshold. Here, the fluidic structures may be designed such that the rotational frequency threshold is equal to or greater than 5 Hz, in embodiments of the present invention.

In embodiments of the invention, the functioning principle includes two phases, which are defined by a rotational frequency threshold. In a first phase, the first fluid chamber is filled, and the liquid column is generated therein. In a second phase, the liquid column is emptied into the second fluid chamber.

In the first phase, the radially interior fluid chamber is filled in the case of a low rotational frequency. In embodiments of the invention, liquid may flow along a chamber wall of the first fluid chamber toward the fluidic connection and enclose a gas volume located in the second fluid chamber, due to the interfacial tension there. The cross section of the fluidic connection and the edge region in which the cross section of the fluidic connection transitions to the cross section of the second fluid chamber may be designed such that, with the forces acting in the case of the rotation at the rotational frequency below the rotational frequency threshold, such closure of the gas volume at the fluidic access to the second fluid chamber is achieved. After closing the fluidic connection, the first fluid chamber may then be filled from the outside to the inside, so that a volume proportion substantial for the dosing can be prevented from entering the second fluid chamber before a liquid meniscus closes the access to the second fluid chamber and the interfacial tension occurring there stops the centrifugally driven flow into the second fluid chamber in the case of rotation below the first rotational frequency threshold.

In embodiments of the present invention, the fluidic connection may be formed as a constriction. In embodiments of the invention, the chamber volume of the first fluid chamber, and hence the maximum volume capacity, may be determined by an overflow structure. In embodiments of the invention, excess volume may be sheared off via an overflow. The overflow structure may be formed as a channel at the same time serving as an aliquoting channel.

In the first phase, a liquid column thus is generated in the first fluid chamber in the case of rotation below the rotational frequency threshold. In this first phase, an surface tension at the interface between liquid and gas, as well as a counterpressure acting on the meniscus of the liquid column by way of the gas in the second fluid chamber cause no or only negligible liquid volume with respect to the volume to be dosed to enter the second fluid chamber. The chamber volume of the first fluid chamber, which determines the volume of the liquid column and thus influences the centrifugal force exerted by the liquid column, the chamber volume of the second fluid chamber, which influences the counterpressure generated, and the geometry in the region of the fluidic connection between the fluid chambers may be set such that, apart from the surface tension, the counterpressure is decisive for no liquid to enter the second fluid chamber.

In embodiments, the counterpressure may be regarded as decisive if the rotational frequency threshold, starting from which a flow to the fluidic connection into the second fluid chamber takes place, is at least 5% higher when the second fluid chamber (excluding the access via the fluid connection) comprises no vent, as compared with a case in which the second fluid chamber comprises a further fluid outlet, i.e. a vent. In embodiments, it may be understood by decisive that this difference in the rotational frequency threshold is at least 10%, 20%, 30% or 40%.

After the filling and dosing process in the first phase, in which the liquid column is generated, the rotational frequency is raised above the rotational frequency threshold in a second phase. By the increasing centrifugal field, the meniscus of the liquid column expands further into the second fluid chamber, on the one hand, which compresses the gas enclosed there and hence increases the gas pressure. On the other hand, the centrifugal field of sufficiently high rotational frequency induces a drop break. Such a drop break reduces the static water column pressure on the interface and increases the gas pressure in the chamber. Furthermore, the dynamics of the detachment process destabilizes the interface, so that proportions of the gas volume may rise through the liquid column. Following the destabilization, the system again strives for a pressure equilibrium. Such a droplet formation process may repeat until the volume dosed in the first fluid chamber has reached the second fluid chamber completely. In embodiments of the invention, the rotational frequency may also be increased successively in this second phase.

Embodiments of the present invention thus provide device and methods for handling, and particularly for switching, liquids, which do without intensive aftertreatment of fluidic structures with local hydrophobic areas and without sharp-edged structures fabricated in highly precise way.

Embodiments of the invention may be formed as microfluidic device and methods to transport and control liquid amounts in the nanoliter to milliliter range in controlled manner, wherein a liquid transport may take place in channels having characteristic dimensions in the micometer to millimeter range. In embodiments, the geometry of the fluidic structures may be formed to provide the described functionality in a liquid/gas system, wherein the liquid has an interfacial tension of >0.01 N/m, >0.02 N/m, 0.03 N/m, 0.04 N/m or 0.05 N/m. For example, embodiments of the invention may be formed to provide the described functionality in a blood-plasma/air system.

Embodiments of the present invention thus provide a valve for switching liquids, based on a centrifugally built-up counterpressure and the stabilization of the meniscus at a fluidic connecting piece.

Embodiments of the invention provide a novel aliquoting structure on the basis of such a valve, which allows for metering and aliquoting liquids independently of upstream substances in a reaction chamber (the second fluid chamber). Such upstream substances may, for example, be primers for a polymerase chain reaction.

As it was described, embodiments of the invention provide a centrifugally controlled pneumatic valve structure, which may comprise a radially exterior chamber, a radially interior inlet structure, and a connecting piece representing the single fluidic access to the radially exterior chamber and formed so that a meniscus stabilized by the interfacial tension initially may form in the area of this connecting piece during the filling of the inlet structure. Thereby, a gas-filled pressure chamber may be sealed via the liquid meniscus in the area of the connecting piece, whereupon a centrifugally driven build-up of a liquid column takes place starting at the radially exterior end of the metering structure. Compression of the gas volume may be achieved via rotationally generated pressure of the liquid column, wherein the geometry of the connecting piece may be chosen so that release of the gas connected to the instability of the liquid column occurs only above the rotational speed threshold.

In embodiments, the first fluid chamber may be implemented as a dosing structure, wherein the rotatory movement below the rotational speed threshold causes shear-off of the liquid column stabilized by the valve in the area of the connecting piece at the radially interior end of the first fluid chamber, which may be referred to as metering channel, for volume definition. Such dosing thus may be done independently of the volumes of reagents possibly upstream in the second fluid chamber, which may be referred to as reaction chamber.

Embodiments of the invention provide an aliquoting structure. In embodiments, a plurality of dosing structures may have a distribution channel, which may bring about a defined minimum filling level of the dosing structures via centrifugal and capillary forces or an applied pressure difference, for example. In embodiments, a distribution structure may at least coincide in portions with dosing structures, comparable with WO-A1-2004/083108. In embodiments, the second fluid chambers may represent reaction chambers located on radially fixed positions, i.e. on a concentric line with respect to a rotation axis, for simplified readout. The distribution structure may be formed by a radially falling (sloping) channel. Mutually adapted dosing volumes of a plurality of first fluid chambers may be achieved by balancing different radial lengths of the first fluid chambers by different widths thereof, in embodiments of the invention.

In embodiments of the invention, a controller capable of controlling the rotational frequency of the driving means to pass through suitable frequency courses may be provided for the driving means. For example, the controller may be formed to switch the driving means between a rotational frequency below the rotational frequency threshold and a rotational frequency above the rotational frequency threshold at maximum rotational acceleration, or to gradually increase a rotational frequency from a rotational frequency below the rotational frequency threshold to a rotational frequency above the rotational frequency threshold.

Of course, the rotational frequency in embodiments of the invention does not have to be fixed during the first rotation, but may change as long as it remains below the rotational frequency threshold, and the rotational frequency during the second rotation does not have to be fixed, but may change as long as it remains above the rotational frequency threshold temporarily.

BRIEF DESCRIPTION OF THE DRAWINGS

Embodiments of the present invention will be detailed subsequently referring to the appended drawings, in which:

FIGS. 4a to 4c are schematic cross-sectional illustrations of fluidic structures;

DETAILED DESCRIPTION OF THE INVENTION

Figure 1:
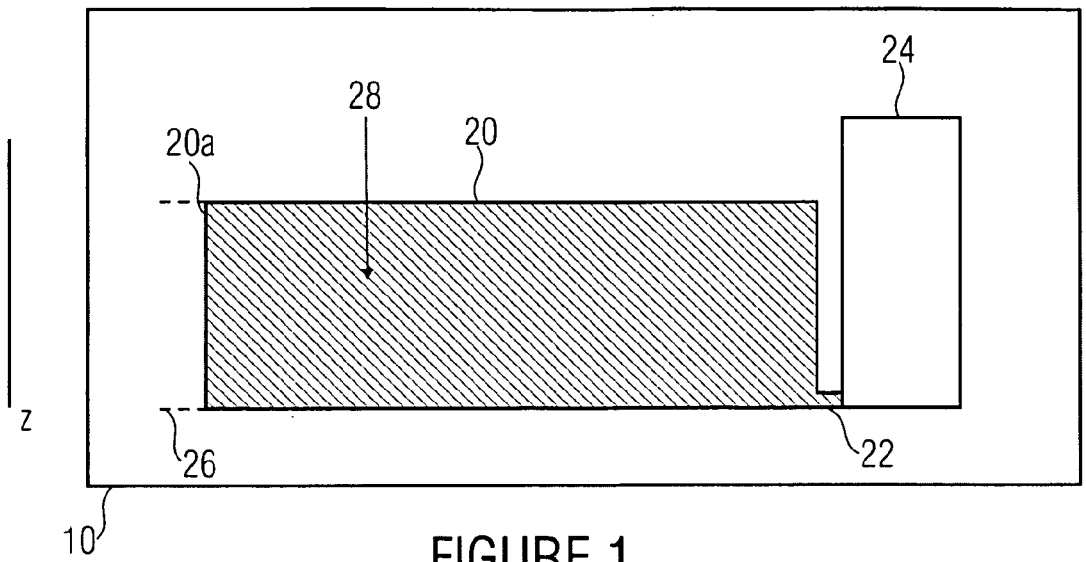
FIG. 1 is a schematic illustration for explaining the principle underlying embodiments of the invention.
Figure 2:
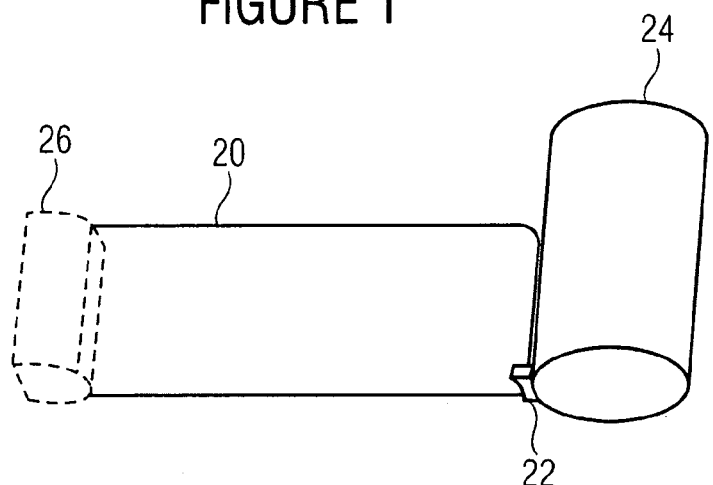
FIG. 2 is a perspective illustration of the structure shown in FIG. 1.

FIG. 1 schematically shows a top view onto an embodiment of a fluidic module in depth profile. Here, the fluidic module 10 is illustrated schematically by a dashed line 10. A perspective view of the fluidic structures formed in the fluidic module 10 is shown in FIG. 2. The fluidic module 10 may be formed as a rotation body with a central rotation axis located within the circumference of the fluidic module. Alternatively, the fluidic module may be a module adapted to be inserted into a matching receptacle of a rotation body, so that the rotation axis is located outside the circumference of the fluidic module.

Figure 3:
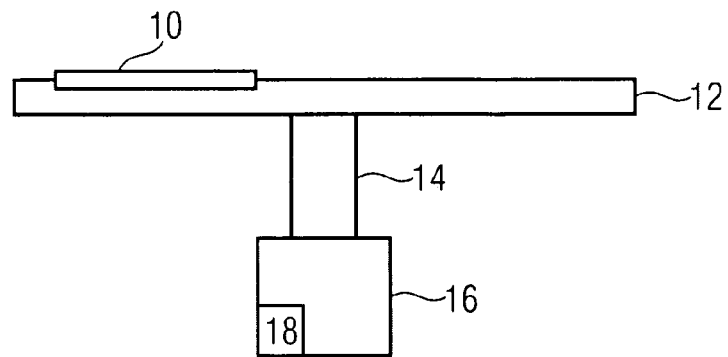
FIG. 3 is a schematic side view of an embodiment of a fluidic device.

FIG. 3 schematically shows a side view of a rotation body 12, into which the fluidic module 10 is inserted. The rotation body 12 may be formed to receive a plurality of fluidic modules 10. Driving means for the rotation body 12 may comprise a substantially conventional construction and include a shaft 14 and a drive motor 16. A controller 18 for the drive motor 16 is formed to cause at least rotation of the fluidic module 10 at a rotational frequency below the described rotational frequency threshold and rotation of the fluidic module 10 at a rotational frequency above the described rotational frequency threshold, in embodiments of the invention.

According to FIGS. 1 and 2, the fluidic structures of the fluidic module 10 include a first fluid chamber 20, a fluidic connection channel 22, and second fluid chamber 24. The first fluid chamber 20 may be filled with a liquid 28 via an inlet structure 26, schematically illustrated by dashed lines, as illustrated by the hatching in FIG. 1. In embodiments, the inlet structure 26 may be formed to cause a defined volume to be introduced into the first fluid chamber 20. To this end, the inlet structure 26 may comprise an overflow structure in known manner or cause shear-off at the radially interior end of the first fluid chamber 20 induced by rotatory movement. FIG. 1 schematically shows a rotation axis Z passing vertically in the illustration, so that a direction from left to right corresponds to a direction from radially interior to radially exterior in FIG. 1.

As can be taken from the depth profile shown in FIG. 1, the fluidic connection 22 has a smaller depth than the first fluid chamber 20 and the second fluid chamber 24, in the embodiment shown, so that the flow cross-section of the fluidic connection 22 is smaller than the flow cross-sections of the first chamber 20 and the second fluid chamber 24 transversal to the flow direction. In general, the fluidic connection has such a cross-section leading into the second fluid chamber that, in an initial filling of the first fluid chamber with the liquid, in the case of rotation at a rotational frequency below the rotational frequency threshold, it is prevented, by the interfacial tension occurring thereat, that liquid reaches the second fluid chamber to a notable extent (of for example more than 10% of the volume of the first fluid chamber).

For filling the first fluid chamber 20 with liquid 28, the fluidic module 10 is subjected to rotation at a rotational frequency below the rotational frequency threshold, so that liquid reaches the fluid chamber 20 via the inlet structure 26. The liquid may for example reach the fluidic connection 22 along a wall of the first fluid chamber 20 and seal a gas volume located in the second fluid chamber 24 via the interfacial tension there. Subsequently, the fluid level rises in the first fluid chamber 20 from radially exterior to radially interior, so that the liquid column shown in FIG. 1 is generated. The first rotational frequency or rotational speed here is such that liquid is prevented from entering the second fluid chamber 24, which may represent a reaction chamber, by the venting exclusively possible via the connection channel 22. If the rotational frequency is raised above the rotational frequency threshold, the pressure on the liquid column becomes greater by way of centrifugation, so that a part thereof pushes ahead far enough into the second fluid chamber 24 and tears off from the rest of the liquid 28. Thereafter, spontaneous partial venting of the chamber in form of an air bubble rising through the connection channel 22 in direction of the rotation center Z through the liquid column takes place. The flat connection channel thus prevents venting of the reaction chamber until the rotational frequency threshold, which may also be referred to as critical rotation frequency, is exceeded and the liquid column tears apart, so that the liquid from the first fluid chamber 20 reaches the second fluid chamber 24.

FIGS. 4a-4c schematically show cross-sectional views of an embodiment of a fluidic structure according to the invention. The fluidic structure includes a distribution channel 30, a first fluid chamber 32, a connecting channel 34, and a second fluid chamber 36. A rotation axis again is designated schematically by Z in FIGS. 4a-4c. FIG. 4a shows a state in which the fluidic module is rotated at a rotational frequency below the rotational frequency threshold. By way of this rotation, a liquid column 38 is formed in the first fluid chamber 32, wherein liquid-filled areas in the figures are illustrated in hatching each. At the rotational frequency below the rotational frequency threshold, the second fluid chamber 36 substantially is empty. A reagent 40 or a microarray may be provided upstream in stationary or liquid manner in the second fluid chamber 36.

FIG. 4b shows a state in the case of rotation at a rotational frequency above the rotational frequency threshold, wherein part of the liquid has emptied into the second fluid chamber 36. FIG. 4c shows a temporally subsequent state in the case of rotation at a rotational frequency above the rotational frequency threshold, wherein the entire liquid content of the first fluid chamber 32 has reached the second fluid chamber 36. So as to introduce a defined liquid volume into the second fluid chamber 36, the volume defined by the second fluid chamber 36 may be equal to or greater than the volume defined by the first fluid chamber 32, in embodiments of the invention.

In embodiments, the first fluid chamber may have a width in a range of 1 mm, a depth in a range of 2 mm and a radial height in a range of 5 mm. The mean radial distance of the first fluid chamber to the rotation center may be 90 mm. The connecting channel 34 may have a radial length in a range of 75 µm, a depth in a range of 200 µm, and a width in a range of 400 µm. The second fluid chamber 36 may have a round shape and have a depth in a range of 3 mm and a diameter in a range of 2 mm. Typical rotational frequencies to achieve the states shown in FIGS. 4a-4c may be at 10 Hz for FIG. 4a, 15 Hz for FIGS. 4b, and 25 Hz for FIG. 4c.

Figure 5:
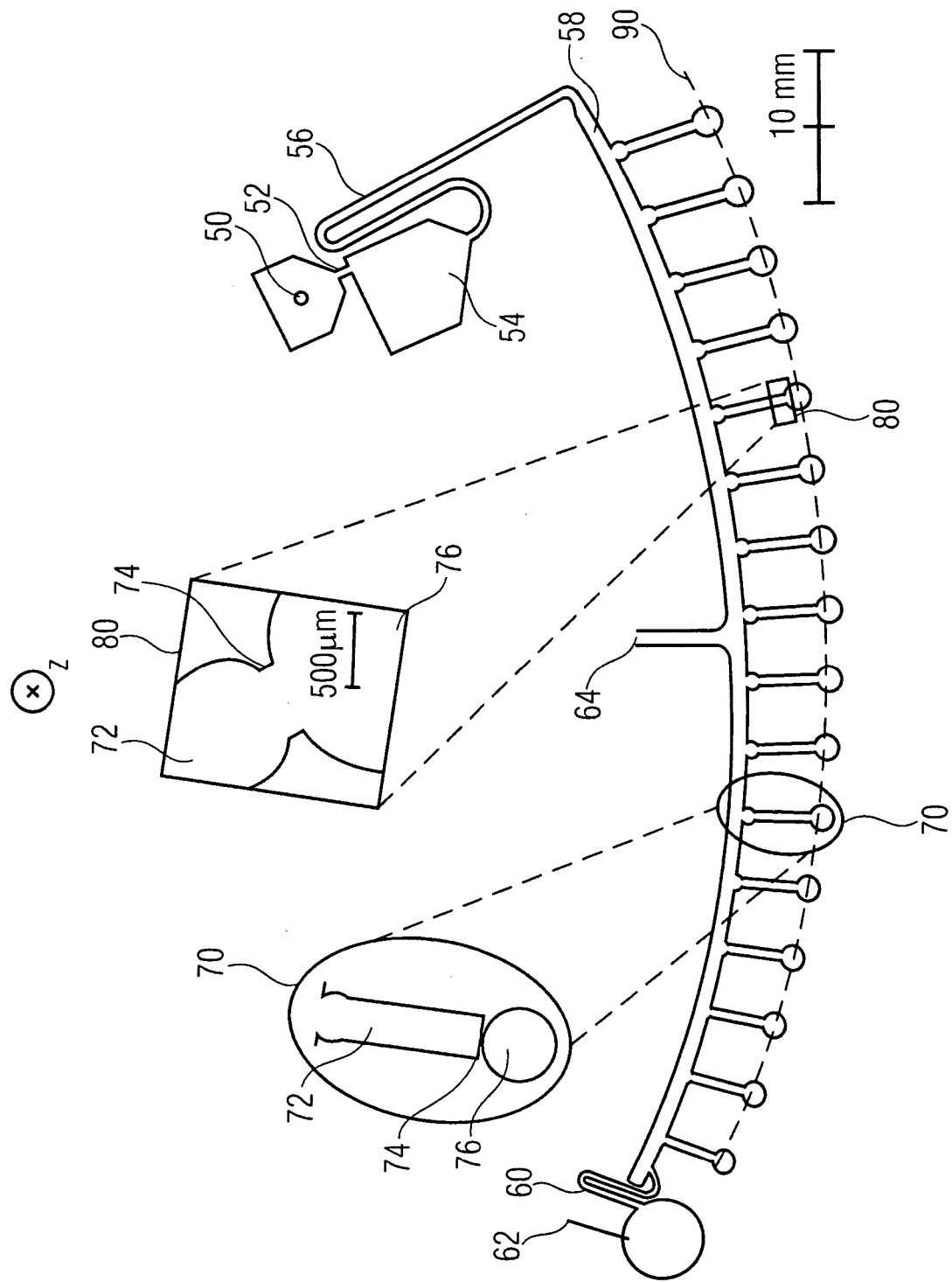
FIG. 5 is a schematic top view of an embodiment of an aliquoting structure.

FIG. 5 schematically shows a top view onto fluidic structures of an embodiment of an aliquoting structure.

Before detailing the embodiments shown in FIG. 5, at first it is to be mentioned that the fluidic structures in embodiments of the invention may be produced corresponding to conventional production techniques using conventional materials, such as plastics, ceramics, glass, silicon, PDMS (polydimethylsiloxane) and other elastomers, and the like. For example, conventional injection-molding methods, micro-milling methods or micromechanical production methods, such as photolithographic methods, may be used for producing the fluidic structures. In embodiments of the invention, the fluidic structures may have a multi-layered construction, wherein the recesses for accommodating fluids are formed in a layer covered by at least a cover layer, wherein vent openings and filling openings may, for example, be provided in the cover layer in suitable fashion.

The aliquoting structure shown in FIG. 5 includes a sample inlet area 50 connected to an inlet chamber 54 via a fluid channel 52. The inlet chamber 54 is connected to an inlet end of a distribution channel 58 via a first siphon channel 56. An outlet end of the distribution channel 58 is fluidically connected to an overflow chamber 62 via a second siphon channel 60. The distribution channel 58 comprises a vent opening 64. A plurality of fluidic structures 70, each of which is illustrated in enlarged manner in FIG. 5, are fluidically connected to the distribution channel 58. Each of the fluidic structures 70 includes a metering channel 72, a connecting channel 74, and a reaction chamber 76. The metering channel 72 here represents a first fluid chamber, the reaction chamber 76 represents a second fluid chamber, and the connecting channel 74 represents a fluidic connection between the chambers 72 and 76. Basically, the construction of the fluidic structures 70 may correspond to the construction described with respect to FIGS. 4a-4c. A reagent (not shown in FIG. 5) may be arranged in at least one, several or all reaction chambers 76.

FIG. 5 further shows an enlargement 80 of the area of the connecting channel 74. As can be taken from the enlargement 80, the connecting channel 74 includes a smaller flow cross-section than adjoining areas of the first fluid chamber 72 and the second fluid chamber 76. At this point, however, it is to be pointed out that highly precisely fabricated structures with sharp edges are not needed here, since, apart from an interfacial tension, to achieve initial closure of the gas volume in the second fluid chamber, the counterpressure exerted by the gas located in the second fluid chamber is decisive for the fact that no liquid enters the second fluid chamber in the case of rotation at a rotational frequency below the rotational frequency threshold.

The distribution channel 58 has a radially falling course with respect to a rotation axis, which is again shown schematically at Z in FIG. 5. More specifically, the distribution channel 58 passes substantially azimuthally, but has a radial component in flow direction, so that liquid can be driven therethrough by centrifugal force. The fluidic structures 70 lead into a radially exterior area of the distribution channel 58 in azimuthally distributed manner. The reaction chambers 76 of the fluidic structures 70 are arranged at a constant radial position, as indicated by the circular arc line 90 arranged concentrically around the rotation axis Z. So as to allow for dosing equal liquid volumes each along the distribution channel in this construction, the metering chambers 72 in the embodiment shown comprise different widths (i.e. dimensions in azimuth direction) to compensate for different lengths of the metering chambers occurring due to the radially falling course of the distribution channel 58. Example scales for the structures shown are illustrated in FIG. 5. The structures may, for example, have dimensions so as to aliquote liquid amounts in the range of 100 µl. Furthermore, the structures are formed so as to enable operation as a pneumatic back-pressure valve, as described above for example with respect to FIGS. 1 and 2.

In operation, at first liquid is introduced into the inlet chamber 54 via the sample inlet area 50. Here, rotation takes place at such a rotational frequency that a centrifugal force in the first siphon structure 56 exceeds a capillary force and the siphon hence does not fill. Then, the rotational frequency is reduced so that the capillary force exceeds the centrifugal force and the channel of the siphon structure 56 fills capillarily. As soon as the liquid meniscus is radially outside the liquid meniscus in the inlet chamber 54, the rotational frequency may be increased again, if required, so as to be able to centrifugally fill the distribution channel 58 and the metering chambers 72. Here, the metering chambers fill with liquid, which displaces the gas, such as air, in the metering chambers toward the distribution channel, in the case of the low rotational frequency.

Figure 6A:
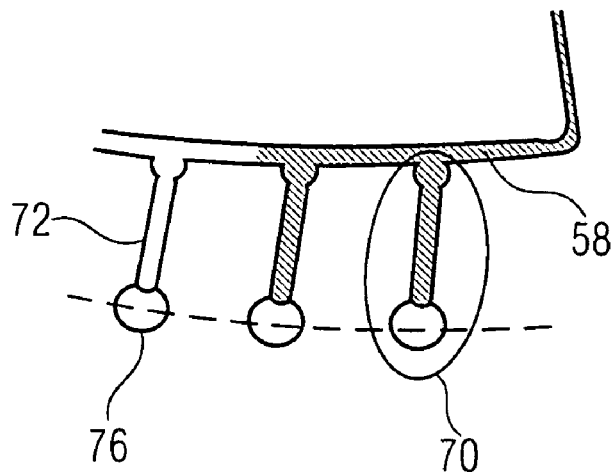
FIGS. 6a to 6c are schematic views of different filling phases of the structure shown in FIG. 5.
Figure 6B:
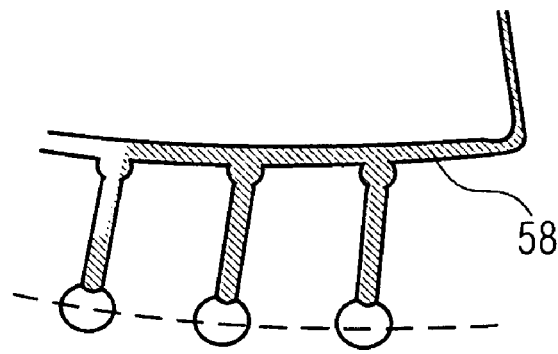
Figure 6C:
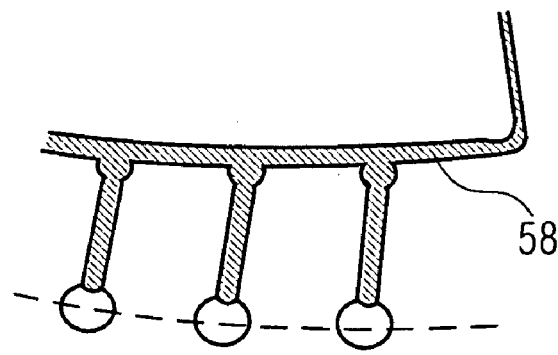

Different phases of such a filling process are shown in FIGS. 6a-6c, in which liquid-filled areas again are illustrated in hatching.

In the state shown in FIG. 6a, the first two metering chambers 72 are filled with liquid, while the third metering chamber 72 is not yet filled. FIG. 6b shows a state in which the third metering chamber is being filled, so that a liquid column is generated there. In the example shown in FIG. 6c, the third metering chamber also is filled with liquid. This filling takes place at such a rotational frequency that gas located in the reaction chambers 76, for example air, has the effect of a pneumatic back-pressure valve, so that the liquid with which the metering chambers 72 are filled does not enter the reaction chamber 76. This filling may for example take place at a rotational frequency of 10 Hz. If all metering channels 72 are filled, an excess of liquid is drained into the overflow chamber 62 via the siphon structure 60. Here, shearing off the liquid at the radially interior ends of the metering chambers 72 takes place in a manner induced by the rotatory movement, so that a defined given liquid volume has been dosed into each of the metering chambers. If a siphon structure 60 is present between the overflow chamber 62 and the distribution channel 58, like in the embodiment shown, the rotational frequency may be controlled correspondingly so as to make capillarily overcoming the siphon structure possible.

As already described, the radial shortening of the metering channels necessitated by the falling distribution channel is compensated by broadening to obtain the same volumes in all metering channels, in the embodiments shown.

In a phase following the filling, the rotational frequency is increased to a value above the rotational frequency threshold, so that the valves break through and the reaction chambers 76 are filled with the liquid located in the metering chambers 72. The rotational frequency threshold here is given by the rotational frequency at which the liquid column becomes unstable, so that at least part of the liquid reaches the reaction chamber. In embodiments, the second rotational frequency is such that the entire liquid from the metering chambers 72 reaches the reaction chambers 76. This second rotational frequency may be 25 Hz, for example.

In embodiments of the invention, aliquoting hence takes place in two phases, wherein metering takes place by shearing off a supernatant in a first phase, and a break-through into a reaction chamber in a second phase. Thus, clean fluidic separation can be obtained for avoiding cross-contaminations of reagents. Furthermore, an equal liquid volume each may be introduced into the reaction chambers, independently of the fact whether different reagent volumes are present in the reaction chambers. Finally, embodiments of the invention also allow for reliably switching buffers with surfactants, since the pneumatic action of a gas back pressure is decisive for the fact that no liquid enters the second fluid chamber at a first rotational frequency. In other words, the fluidic structures consisting of first fluid chamber, fluidic connection, and second fluid chamber represent rotatorily switched pneumatic back-pressure valves.

In embodiments of the invention, the overflow chamber may be replaced by a fluid chamber also connected to the distribution channel via a pneumatic valve, but having a lower breakdown frequency than the valve associated with the reaction chambers. Alternatively, a dummy structure corresponding to the structures 70 except for a lower breakdown frequency could be provided between the last reaction chamber and the overflow chamber. An effect in that the first (rightmost) reaction chamber shows a higher filling level and the last (leftmost) reaction chamber shows a lower filling level can be reduced or ideally prevented by such structures.

In embodiments of the invention, the fluidic structures may be milled into a COP (Cyclo-Olefin-Polymer) body. To make the channels hydrophilic, they may be coated with polyethylene glycol. The body thus treated may be provided with a suitable lid, for example a two-layered foil, as it is described in J. Steigert et al., "Rapid prototyping of microfluidic chips in COC", Journal of Micromechanics and Microengineering, Vol. 17, No. 2, p. 333-341, February 2007.

In embodiments of the invention, the outlet of the first fluid chamber may be formed by several outlets, and the fluidic access of the second fluid chamber may be formed by several inlets. A respective inlet may then be connected to a respective outlet via a fluidic connection. The resultant overall structure may be designed such that it acts as a rotatorily switched pneumatic back-pressure valve. In embodiments of the invention, the second chamber does not have to be arranged completely radially outside the first chamber, as long as the centrifugal pressure needed for reaching a centrifugal drive can be reached.

Regarding the functionality of the inventive approach to solution, measurements with ink-containing water with metering channel lengths ranging from 3.08 mm to 5.36 mm and varying connecting channel depths ranging from 60 to 400 μm were performed.

A centrifugal pressure $P_{centrifugal}$ present in the connecting channel, generated by the liquid column and determined by centrifugation can be calculated from the rotational frequency v according to $$p_{centrifugal} = (2\pi v)^2 \times l \times r \times \rho,$$

wherein l is the length of the liquid column, r is the mean radial position thereof, and ρ is the density of water.

When using water, the valve showed breakdown at centrifugal pressures between 6,700 Pa and 2,100 Pa, wherein variations of the centrifugal pressure at which the breakdown took place were between 28% and 37%, associated with tolerances of the milling process.

In order to verify the pneumatic principle, vent openings preventing the build-up of pneumatic pressure were created in the reaction chambers. This reduced the centrifugal pressures by a factor of 4 or more as compared with the original structures without vent openings. Moreover, the small influence of capillary forces and/or surface tensions could be verified by adding the detergent Tween 20 (0.1% v/v) to reduce surface tension. Although the centrifugal pressures were reduced as compared with water, the liquid can still be switched reliably.

Figure 7:
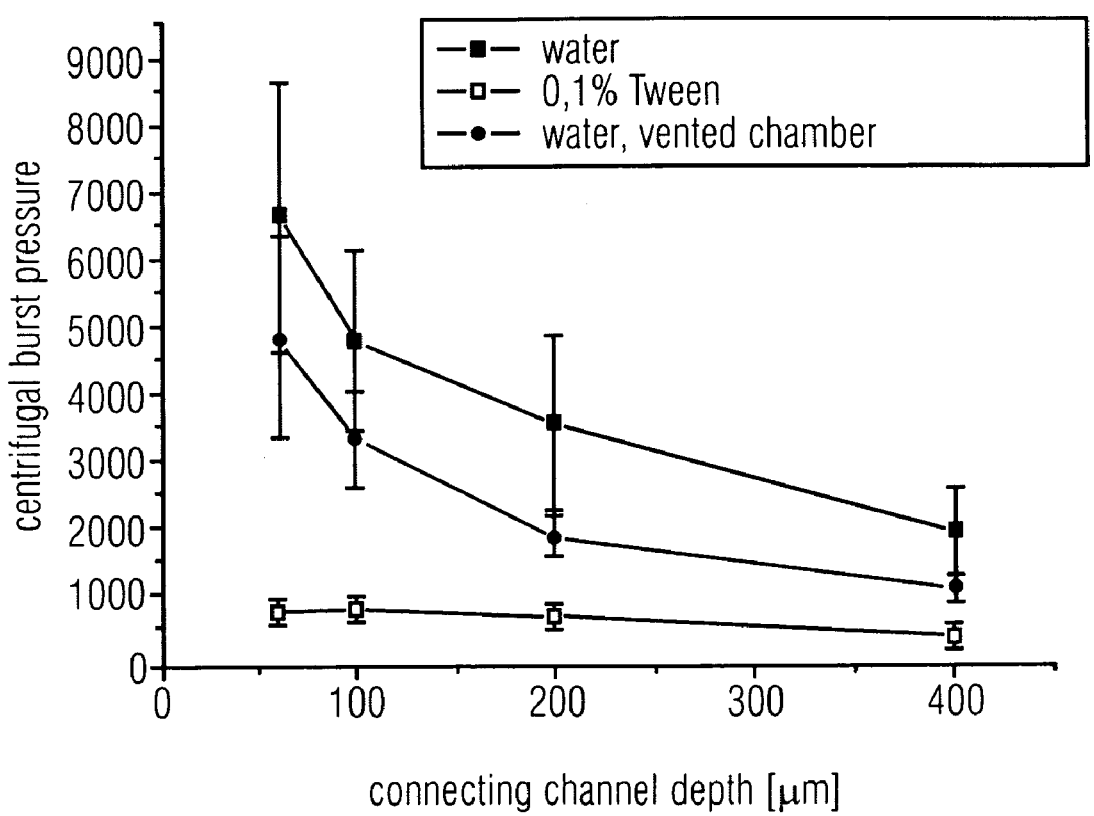
FIG. 7 shows graphs illustrating the effect of the pneumatic pressure.

The results of the measurements are illustrated in FIG. 7, which shows the dependence of the centrifugal pressure at which the breakdown took place on the depth of the narrow connecting channel. The respective vertical bars show the standard deviations. The low centrifugal pressures for vented reaction chambers clearly show that capillary actions are negligible as compared with the effect of the pneumatic pressure.

Finally, it will be dealt with the theory underlying the pneumatic valve. Effects relating to the instability of an interface between two media in a gravity-like field generally are referred to as Rayleigh-Taylor instabilities. According to D. H. Sharp, "An Overview of Rayleigh-Taylor Instability", Physica D, Vol. 12, No. 1-3, p. 3-18, 1984, a mathematically idealized, unlimited interface between two liquids in a gravitational field is unstable if the denser liquid lies above the less dense liquid. Nevertheless, the surface tension stabilizes periodic disturbances of the interface if the wavelength of the periodic disturbances (surface waves) is smaller than a critical wavelength $\lambda_{crit}$. The critical wavelength can be calculated as $$\lambda_{crit} = 2\pi \sqrt{\sigma/[G(\rho_H - \rho_L)]},$$

wherein σ is the surface wave tension, G is the acceleration of the gravitational field, and $\rho_H$ and $\rho_L$ are the densities of the denser and less dense liquids, respectively.

This approximation applies for incompressible liquids, wherein the correction for compressible media is small, however, according to M. S. Plesset et al., "General Analysis of the Stability of Superposed Fluids", Physics of Fluids, Vol. 7, No. 8, p. 1099-1108, 1964, so that this formula may be used approximately for an interface between a liquid and a gas, and hence for a centrifugal-pneumatic valve. Critical wavelengths calculated for such a system lie on the order of the connection channel geometries, which is an indicator for the fact that the system substantially behaves like a Rayleigh-Taylor instability between two liquids. However, the effect of limited spatial expansion and the curvature of the meniscus in their systems considered as opposed to an infinitely expanded, planar interface, which underlies the above equation of the critical wavelength, are not taken into account in this estimation.

The relevant forces may be estimated as follows. Gas, such as the air contained in the closed reaction chamber, follows the ideal gas equation of $$p_{gas} V = nRT,$$

in good approximation under atmospheric conditions, wherein $p_{gas}$ is the pressure, V the volume, n the number mol of gas, R the gas constant, and T the temperature. In the case of a reduction of the available volume V, the pressure $p_{gas}$ increases at constant temperature. Thus, if the liquid column in the first fluid chamber enters the second fluid chamber through the connecting channel, it compresses the gas there and thus increases the pressure in the reaction chamber. This prevents further liquid from entering.

The capillary pressure also stabilizes the liquid at the connecting piece. The capillary pressure corresponds to $$p_{capillary} = k \cdot \sigma \cdot \cos \theta,$$

with k as the mean curvature of the liquid interface (=2/r in a sphere), σ as the surface tension, and θ as the contact angle between the liquid and the material of the surface of the connecting piece.

As described above, a pressure $p_{centrifugal}$ generated by the liquid column and determined by centrifugation is present at the connecting piece.

If the centrifugal pressure $p_{centrifugal}$ increases, the liquid meniscus further penetrates the reaction chamber until the gas pressure $p_{gas}$ increased thereby compensates the pressure $P_{centrifugal}$ and the reduced curvature k. If the liquid column has entered far enough into the chamber, part of the liquid tears off, as it is described in J. Eggers, "Tropfenbildung", Phys. Bl., Vol. 53, p. 431-434, 1997, part of the gas may escape in form of an air bubble, passing the receding meniscus. Thereby, the pressure in the chamber decreases in accordance with the above ideal gas equation, and the process starts again.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A fluidic device, comprising:
a fluidic module comprising a first fluid chamber with a fluid outlet, a second fluid chamber with a fluidic access, and a fluidic connection between the fluid outlet of the first fluid chamber and the fluidic access of the second fluid chamber, wherein the second fluid chamber is fluidically connected only to the first fluid chamber and otherwise is fluidically closed; and a drive formed to impart the fluidic module with a first rotation at a rotational frequency below a rotational frequency threshold and a second rotation at a rotational frequency above the rotational frequency threshold, wherein the first and second fluid chambers and the fluidic connection are formed such that, in the case of rotation at a rotational frequency below the rotational frequency threshold, a fluidic closure is formed by the liquid at the fluidic access to the second fluid chamber, and a liquid column comprising a radially exterior meniscus on which gas located in the second fluid chamber exerts a back pressure decisive for the liquid column to remain stable is generated in the first fluid chamber, and in the case of rotation at a rotational frequency above the rotational frequency threshold, the liquid column becomes unstable so that liquid enters the second fluid chamber and gas escapes through the liquid column.

2. The fluidic device according to claim 1, wherein the fluidic connection comprises a connecting channel comprising a flow cross-section smaller than a cross-section of the first fluid chamber transversal to the flow direction and a cross-section of the second fluid chamber transversal to the flow direction.

3. The fluidic device according to claim 1, wherein the first fluid chamber comprises a first chamber volume and the second fluid chamber a second chamber volume greater than or equal to the first chamber volume.

4. The fluidic device according to claim 1, wherein the fluidic module comprises an overflow fluidically connected to the first fluid chamber such that the liquid column is generated with a defined volume in the case of the first rotation.

5. The fluidic device according to claim 1, wherein the first fluid chamber comprises a radially interior end fluidically connected to a fluid channel, comprising azimuthal components in flow direction, so that shearing off the liquid column at the radially interior end of the first fluid chamber takes place by the first rotation after generating the liquid column in the first fluid chamber.

6. The fluidic device according to claim 1, comprising a plurality of azimuthally distributed fluidic structures each comprising a first fluid chamber, a fluidic connection, and a second fluid chamber.

7. The fluidic device according to claim 6, wherein radially interior ends of the first fluid chambers of the fluidic structures are fluidically connected to a common distribution channel.

8. The fluidic device according to claim 7, wherein the common distribution channel is a radially falling channel.

9. The fluidic device according to claim 6, wherein the plurality of second fluid chambers of the fluidic structures are arranged on a line concentrical with a rotation axis about which the fluidic module is rotatable.

10. The fluidic device according to claim 6, wherein the plurality of azimuthally distributed first fluid chambers of the fluidic structures comprise different lengths in radial direction, wherein a first fluid chamber longer in radial direction comprises a smaller width in azimuthal direction, in order to adapt the chamber volumes of the first fluid chambers to each other.

11. The fluidic device according to claim 1, wherein a reagent or a micro-array is arranged in the second fluid chamber.

12. The fluidic device according to claim 1, wherein the second rotation takes place at such a rotational frequency that the entire volume of the liquid column enters the second fluid chamber.

13. The fluidic device according to claim 1, wherein the second rotation takes place at such a rotational frequency that only a partial volume of the liquid column enters the second fluid chamber.

14. A fluidic module for a fluidic device according to claim 1, comprising:
a first fluid chamber with a fluid outlet;
a second fluid chamber comprising a fluidic access;
a fluidic connecting channel between the fluid outlet of the first fluid chamber and the fluidic access of the second fluid chamber,
wherein the second fluid chamber is fluidically connected only to the first fluid chamber and otherwise is fluidically closed,
wherein the first and second fluid chambers and the fluidic connection are formed such that,
in the case of rotation at a rotational frequency below the rotational frequency threshold, a fluidic closure is formed by the liquid at the fluidic access to the second fluid chamber, and a liquid column comprising a radially exterior meniscus on which gas located in the second fluid chamber exerts a back pressure decisive for the liquid column to remain stable is generated in the first fluid chamber, and
in the case of rotation at a rotational frequency above the rotational frequency threshold, the liquid column becomes unstable so that liquid enters the second fluid chamber and gas escapes through the liquid column,
wherein there are provided a plurality of azimuthally distributed fluidic structures each comprising a first fluid chamber, a fluidic connection, and a second fluid chamber,
wherein radially interior ends of the first fluid chambers of the fluidic structures are fluidically connected to a common radially falling distribution channel,
wherein the plurality of second fluid chambers of the fluidic structures are arranged on a line concentrical with a rotation axis about which the fluidic module is rotatable, and
wherein the plurality of azimuthally distributed first fluid chambers of the fluidic structures comprise different lengths in radial direction, wherein a first fluid chamber longer in radial direction comprises a smaller width in azimuthal direction, in order to adapt the chamber volumes of the first fluid chambers to each other.

15. The fluidic module according to claim 14, comprising a rotation body with a rotation-symmetric shape and a central rotation axis.

16. The fluidic module according to claim 14, which is adapted to be inserted into a matching receptacle of a rotation body.

17. The fluidic module according to claim 14, wherein the first and second fluid chambers and the fluidic connection are formed such that the rotational frequency threshold is equal to or greater than a rotational frequency of 5 Hz.

18. A method of handling a liquid in a fluidic module comprising a first fluid chamber with a fluid outlet, a second fluid chamber with a fluid access, and a fluidic connection between the fluid outlet of the first fluid chamber and the fluidic access of the second fluid chamber, wherein the second fluid chamber is radially connected only to the first fluid chamber and otherwise is fluidically closed, comprising:

rotating the fluidic module at a rotational frequency below a rotational frequency threshold for creating a fluidic closure by the liquid at the fluidic access to the second fluid chamber and for creating a liquid column in the first fluid chamber, which comprises a radially exterior meniscus, on which gas located in the second fluid chamber exerts a back pressure decisive for the liquid column to remain stable; and then rotating the fluidic module at a rotational frequency above the rotational frequency threshold such that the liquid column becomes unstable so that liquid enters the second fluid chamber and gas escapes through the liquid column.

19. The method according to claim 18, wherein, when rotating at a rotational frequency below the rotational frequency threshold, a liquid column with a defined volume, which reaches the second fluid chamber completely when rotating at a rotational frequency above the rotational frequency threshold, is created in the first fluid chamber.

20. The method according to claim 18, wherein, when rotating at a rotational frequency below the rotational frequency threshold, liquid columns in a plurality of azimuthally distributed first fluid chambers are created, which are fluidically connected to a plurality of azimuthally distributed second fluid chambers via a plurality of fluidic connections, wherein liquid enters the plurality of second fluid chambers when rotating at a rotational frequency above the rotational frequency threshold.

* * * * *